(12) United States Patent
Behera et al.

(10) Patent No.: US 12,011,229 B2
(45) Date of Patent: Jun. 18, 2024

(54) SYSTEM AND METHOD FOR PROVIDING VISUAL GUIDANCE IN A MEDICAL SURGERY

(71) Applicant: HCL TECHNOLOGIES LIMITED, New Delhi (IN)

(72) Inventors: Sanjeeb Kumar Behera, Bangalore (IN); Karthik Balasubramanian, Chennai (IN); Dipumon Ayyanchira Mani, Bangalore (IN); Yoganand Ramalingam, Chennai (IN); Pankaj Arunrao Pinjarkar, Bangalore (IN); Peram Balakrishna, Chennai (IN)

(73) Assignee: HCL TECHNOLOGIES LIMITED, New Delhi (IN)

( * ) Notice: Subject to any disclaimer, the term of this patent is extended or adjusted under 35 U.S.C. 154(b) by 835 days.

(21) Appl. No.: 17/031,556

(22) Filed: Sep. 24, 2020

(65) Prior Publication Data
US 2022/0015835 A1 Jan. 20, 2022

(30) Foreign Application Priority Data
Jul. 15, 2020 (IN) .............................. 202011030082

(51) Int. Cl.
*A61B 34/20* (2016.01)
*A61B 34/00* (2016.01)
(Continued)

(52) U.S. Cl.
CPC .............. *A61B 34/20* (2016.02); *A61B 34/10* (2016.02); *A61B 34/25* (2016.02); *A61B 90/90* (2016.02);
(Continued)

(58) Field of Classification Search
CPC ......... A61B 34/10; A61B 34/25; A61B 90/90; A61B 2034/102; A61B 2034/105; A61B 2034/252; A61B 34/20; G06F 3/011
See application file for complete search history.

(56) References Cited

U.S. PATENT DOCUMENTS 10,010,379 B1  7/2018  Gibby et al.
10,194,131 B2  1/2019  Casas
(Continued)

FOREIGN PATENT DOCUMENTS

WO  2015110859 A1  7/2015
WO  2017016065 A1  2/2017
WO  2019070681 A1  4/2019

OTHER PUBLICATIONS

Boehler, L. U. K. A. S., Daniol, M. A. T. E. U. S. Z., & Wehrle, C. H. R. I. S. T. I. A. N. (2016). Identification of instruments and implants with RFID and Data Matrix Codes for the use at the instrument table. Przeglad Elektrotechniczny, 1(11), 227-230. (Year: 2016).*

*Primary Examiner* — Bijan Mapar

(57) ABSTRACT

Disclosed is a method for providing visual guidance in a medical surgery. The method comprises registering, within a virtual assistance device having a combination of a virtual medical implant, an Intra-Medullary (IM) nail model and a virtual insertion handle model, each of a physical IM nail implant and a physical insertion handle. Further, a physical drill gun is registered within the virtual assistance device having a drill gun model. Further, coordinates of the one or more holes on the physical IM nail implant are registered within the virtual assistance device. The physical IM nail is inserted into a target. The virtual impression of the physical drill gun is aligned over the one or more holes based on the coordinates. Further, one or more surgical steps are performed by the physical drill gun based on the aligning.

18 Claims, 19 Drawing Sheets

(51) Int. Cl.
*A61B 34/10* (2016.01)
*A61B 90/90* (2016.01)
*G06F 3/01* (2006.01)

(52) U.S. Cl.
CPC ........ *G06F 3/011* (2013.01); *A61B 2034/102* (2016.02); *A61B 2034/105* (2016.02); *A61B 2034/252* (2016.02)

(56) References Cited

U.S. PATENT DOCUMENTS

2017/0258526 A1* 9/2017 Lang .................. A61B 17/1775
2021/0307842 A1* 10/2021 May ....................... A61B 5/064

* cited by examiner

SYSTEM AND METHOD FOR PROVIDING VISUAL GUIDANCE IN A MEDICAL SURGERY

CROSS-REFERENCE TO RELATED APPLICATIONS AND PRIORITY

The present application claims priority from Indian Patent Application No. 202011030082 filed on 15 Jul. 2020, the entity of which is hereby incorporated by reference.

TECHNICAL FIELD

The present disclosure in general relates to the field of mixed reality. More particularly, the present invention relates to a system and method for providing visual guidance in a medical surgery.

BACKGROUND

Generally, surgeries in current orthopaedics practices are performed in an Operating Room (OR) setting equipped with an X-ray imaging device such as fluoroscopy. An example of such kind of a surgery is using tibial/femoral nail intended for stabilizing fractures of proximal, distal shaft and closed shaft fractures. The tibial/femoral nail is implanted inside a patient through a surgical procedure. The surgical procedure is executed by an orthopaedic surgeon in the OR setting equipped with the X-ray imaging device.

The general practices in Intra Medullary (IM) nail surgeries are dependent on multiple X-ray scanning with trial and error based methods. The X-ray scanning procedure performed multiple times leads to increase in cost of the surgery and health risk associated with the patient. Further, the trial and error based methods are time-consuming leading to an increase in anaesthesia duration for the patient and ultimately increasing the health risk for the patient, surgeon and associated staff. In addition, the manual processes of performing surgeries have more dependency on the surgeon's skills and judgement leading to errors & prolonged surgery duration.

SUMMARY

Before the present system and method for providing visual guidance in a medical surgery is described, it is to be understood that this application is not limited to the particular systems, and methodologies described, as there can be multiple possible embodiments which are not expressly illustrated in the present disclosure. It is also to be understood that the terminology used in the description is for the purpose of describing the particular versions or embodiments only, and is not intended to limit the scope of the present application. This summary is provided to introduce concepts related to the system and method for providing visual guidance in a medical surgery. This summary is not intended to identify essential features of the claimed subject matter nor is it intended for use in determining or limiting the scope of the claimed subject matter.

In one implementation, a method for providing visual guidance in a medical surgery is illustrated. The method may comprise registering, within a virtual assistance device having a combination of a virtual medical implant, an Intra-Medullary (IM) nail model and a virtual insertion handle model, a construct having at least one of a physical IM nail implant and a physical insertion handle. The registering may be performed by scanning a first QR code attached to the physical insertion handle. The first QR code may be sensed by the virtual assistance device. The virtual IM nail model may create a virtual impression of the physical IM nail implant and the physical insertion handle within the virtual assistance device. The method may further comprise registering, within the virtual assistance device having a drill gun model, a physical drill gun by scanning a second QR code attached to the physical drill gun. The drill gun model may create a virtual impression of the physical drill gun within the virtual assistance device. The method may further comprise inserting, one or more third QR codes into one or more hole(s) provided over the physical IM nail implant. The one or more holes may be provided for accepting screws during the medical surgery. The method may further comprise registering through the one or more third QR codes, within the virtual assistance device, coordinates of the one or more holes with respect to the coordinates of the virtual impression of the physical IM nail implant and the physical insertion handle. The method may further comprise inserting, each of the physical IM nail implant and the physical insertion handle into a target. The method may further comprise displaying, over the virtual assistance device, each of the virtual impression of the physical IM nail implant inside the target, the virtual impression of the physical drill gun, and the coordinates of the one or more holes. The method may further comprise positioning, the virtual impression of the physical drill gun over the virtual impression of the physical IM nail implant inside the target. The method may further comprise aligning, the virtual impression of the physical drill gun over the one or more holes based on the coordinates of the one or more holes registered within the virtual assistance device. The aligning may guide movement of the physical drill gun over the target in real-time. The method may further comprise performing through the physical drill gun, one or more surgical steps over the target based on the aligning.

In another implementation, a system for providing visual guidance in a medical surgery is illustrated. The system may comprise a virtual assistance device having a combination of a virtual medical implant, an Intra-Medullary (IM) nail model and a virtual insertion handle model. The virtual assistance device may be configured for registering, within the virtual assistance device, a construct having at least one of a physical IM nail implant and a physical insertion handle. The registering may be performed by scanning a first QR code attached to the physical insertion handle. The first QR code may be sensed by the virtual assistance device. The virtual IM nail model may create a virtual impression of the physical IM nail implant and the physical insertion handle within the virtual assistance device. The virtual assistance device may be further configured for registering, within the virtual assistance device having a drill gun model, a physical drill gun by scanning a second QR code attached to the physical drill gun. The drill gun model may create a virtual impression of the physical drill gun within the virtual assistance device. The virtual assistance device may be further configured for registering within the virtual assistance device, through one or more third QR code(s) inserted on one or more holes, coordinates of one or more holes with respect to the coordinates of the virtual impression of the physical IM nail implant and the physical insertion handle. The one or more hole(s) may be provided over the physical IM nail implant for accepting screws during the medical surgery. The virtual assistance device may be further configured for displaying, over the virtual assistance device, each of the virtual impression of the physical IM nail implant inside the target, the virtual impression of the physical drill gun, and the coordinates of the one or more holes while inserting, each of the physical IM nail implant and the physical insertion handle into a target. The virtual assistance device may be further configured for positioning, the virtual impression of the physical drill gun over the virtual impression of the physical IM nail implant inside the target. The virtual assistance device may be further configured for aligning, the virtual impression of the physical drill gun over the one or more holes based on the coordinates of the one or more holes registered within the virtual assistance device. The aligning may guide movement of the physical drill gun over the target in real-time while performing one or more surgical steps over the target through the physical drill gun.

In yet another implementation, a virtual assistance device for providing visual guidance in a medical surgery is illustrated. The virtual assistance device may comprise a memory storing each of an Intra-Medullary (IM) nail model, a virtual insertion handle model, and a drill gun model. The virtual assistance device may further comprise a processor configured to execute a set of instructions stored in the memory. Further, the processor may be configured for registering, a construct having at least one of a physical IM nail implant and a physical insertion handle. The registering may comprise scanning a first QR code attached to the physical insertion handle. The first QR code may be sensed by the virtual assistance device. The virtual IM nail model may create a virtual impression of the physical IM nail implant and the physical insertion handle within the virtual assistance device. Further, the processor may be configured for registering, a physical drill gun. The registering may comprise scanning a second QR code attached to the physical drill gun. A drill gun model may create a virtual impression of the physical drill gun within the virtual assistance device. Further, the processor may be configured for registering, through one or more third QR codes inserted on one or more holes provided over the physical IM nail implant for accepting screws during the medical surgery, coordinates of the one or more holes with respect to the coordinates of the virtual impression of the physical IM nail implant and the physical insertion handle. The virtual assistance device may further comprise a user interface. The user interface may be configured for displaying, each of the virtual impression of the physical IM nail implant inside a target, the virtual impression of the physical drill gun, and the coordinates of the one or more holes while inserting, each of the physical IM nail implant and the physical insertion handle into the target. Further, the processor may be configured for positioning, the virtual impression of the physical drill gun over the virtual impression of the physical IM nail implant inside the target. Further, the processor may be configured for aligning, the virtual impression of the physical drill gun over the one or more holes based on the coordinates of the one or more holes registered within the virtual assistance device. The aligning may guide movement of the physical drill gun over the target in real-time while performing one or more surgical steps over the target through the physical drill gun.

In yet another implementation, a method for providing visual guidance in a medical surgery is illustrated. The method may comprise registering, by a processor a construct having at least one of a physical IM nail implant and a physical insertion handle within a virtual assistance device. Further, the registering may comprise scanning a first QR code attached to the physical insertion handle. The first QR code may be sensed by the virtual assistance device. Further, a virtual IM nail model may create a virtual impression of the physical IM nail implant and the physical insertion handle within the virtual assistance device. The method may further comprise registering, by the processor, a physical drill gun. The registering may comprise scanning a second QR code attached to the physical drill gun. Further, a drill gun model may create a virtual impression of the physical drill gun within the virtual assistance device. The method may further comprise registering, by the processor through one or more third QR codes inserted on one or more holes provided over the physical IM nail implant for accepting screws during the medical surgery, coordinates of the one or more holes with respect to the coordinates of the virtual impression of the physical IM nail implant and the physical insertion handle. Further, each of the virtual impression of the physical IM nail implant inside a target, the virtual impression of the physical drill gun, and the coordinates of the one or more holes are displayed on a user interface while inserting, each of the physical IM nail implant and the physical insertion handle into the target. The method may further comprise positioning, by the processor, the virtual impression of the physical drill gun over the virtual impression of the physical IM nail implant inside a target. Further, the method may comprise aligning, by the processor, the virtual impression of the physical drill gun over the one or more holes based on the coordinates of the one or more holes registered within the virtual assistance device. The aligning may guide movement of the physical drill gun over the target in real-time while performing one or more surgical steps over the target through the physical drill gun.

BRIEF DESCRIPTION OF DRAWINGS

The detailed description is described with reference to the accompanying figures. In the figures, the left-most digit(s) of a reference number identifies the figure in which the reference number first appears. The same numbers are used throughout the drawings to refer like features and components.

DETAILED DESCRIPTION

Figure 1A:
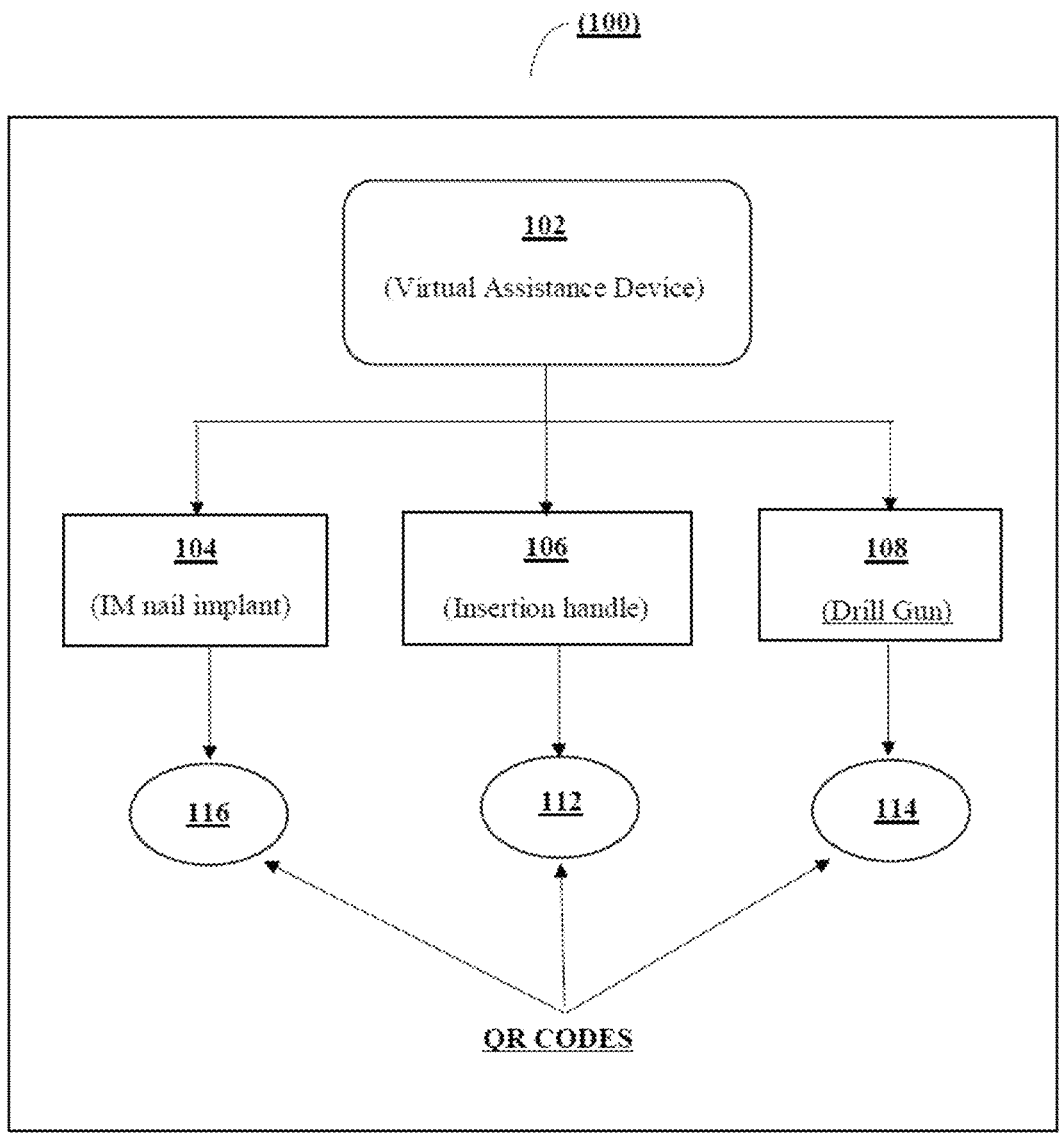
FIGS. 1A and 1B illustrate a system 100 for providing visual guidance in a medical surgery, in accordance with an embodiment of the present subject matter.

Some embodiments of the present disclosure, illustrating all its features, will now be discussed in detail. The words "comprising", "receiving", "determining", "generating" and other forms thereof, are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a", "an" and "the" include plural references unless the context clearly dictates otherwise. Although any systems and methods similar or equivalent to those described herein can be used in the practice or testing of embodiments of the present disclosure, the exemplary system and method for providing visual guidance in a medical surgery are now described. The disclosed embodiments of the system and method for providing visual guidance in a medical surgery are merely exemplary of the disclosure, which may be embodied in various forms.

Various modifications to the embodiment will be readily apparent to those skilled in the art and the generic principles herein may be applied to other embodiments. However, one of ordinary skill in the art will readily recognize that the present disclosure for system and method for providing visual guidance in a medical surgery is not intended to be limited to the embodiments illustrated, but is to be accorded the widest scope consistent with the principles and features described herein.

Typically, current practices in orthopaedic involves surgeries performed in an Operating Room (OR) setting equipped with an X-ray imaging device. An example of such kind of a surgery is using tibial/femoral nail intended for stabilizing fractures of the proximal, distal shaft and closed shaft fractures. The tibial/femoral nail is implanted through a surgical procedure. The surgical procedure is executed by an orthopaedic surgeon in the OR setting equipped with the X-ray imaging device. The conventional practices are dependent on multiple X-ray scanning with trial and error based methods. The X-ray scanning procedure performed multiple times in conventional systems leads to an increase in the cost of the surgery and health risk associated with the patient, surgeon and associated staff. Also, due to the trial and error based methods, the conventional systems are time consuming leading to an increase in anaesthesia duration for the patient and ultimately increasing the health risk for the patient. In addition, the conventional systems have more dependency on the surgeon's skills and judgement leading to errors and prolonged surgery duration. Thus, overall conventional systems may lack efficiency in performing surgical procedures.

The present subject matter overcomes the problems of the conventional systems. The present subject matter relates to a method for providing visual guidance in a medical surgery. The method comprises registering a construct having at least one of a physical IM nail implant and a physical insertion handle, within a virtual assistance device having a combination of a virtual medical implant, an Intra-Medullary (IM) nail model and a virtual insertion handle model. The registering may be performed by scanning a first QR code attached to the physical insertion handle. The first QR code may be sensed by the virtual assistance device. In addition, the virtual IM nail model may create a virtual impression of the physical IM nail implant and the physical insertion handle within the virtual assistance device.

The method further comprises registering a physical drill gun by scanning a second QR code attached to the physical drill gun, within the virtual assistance device having a drill gun model, The drill gun model may create a virtual impression of the physical drill gun within the virtual assistance device. Further, one or more third QR codes may be inserted into one or more hole(s) provided over the physical IM nail implant. The one or more holes may be provided for accepting screws during the medical surgery. The method further comprises registering coordinates of the one or more holes with respect to the coordinates of the virtual impression of the physical IM nail implant and physical insertion handle through the one or more third QR codes, within the virtual assistance device. Further, each of the physical IM nail implant and the physical insertion handle may be inserted into a target. Furthermore, each of the virtual impression of the physical IM nail implant inside the target, the virtual impression of the physical drill gun, and the coordinates of the one or more holes may be displayed, over the virtual assistance device.

The method further comprises positioning, the virtual impression of the physical drill gun over the virtual impression of the physical IM nail implant inside the target. Further, the virtual impression of the physical drill gun may be aligned over the one or more holes based on the coordinates of the one or more holes registered within the virtual assistance device. The aligning may guide movement of the physical drill gun over the target in real-time. The method further comprises performing, through the physical drill gun, one or more surgical steps over the target based on the aligning.

The present subject matter is based on the method for providing visual guidance in a medical surgery a through virtual assistance device, thereby eliminating the multiple X-ray scanning procedure and trial and error-based method. The method provides life size augmented virtual models for seamless user experience to the medical practitioner (surgeon). The method reduces dependency on the medical practitioner's skills and visual judgment, thereby increasing accuracy of the surgical procedure. Also, due to the elimination of X-ray scanning procedure, the cost of the surgery, time consumption, and health risk associated with the patient is reduced.

It is to be noted that the present subject matter may lead to an overall improvement in the surgical procedure by providing visual guidance.

Figure 1B:
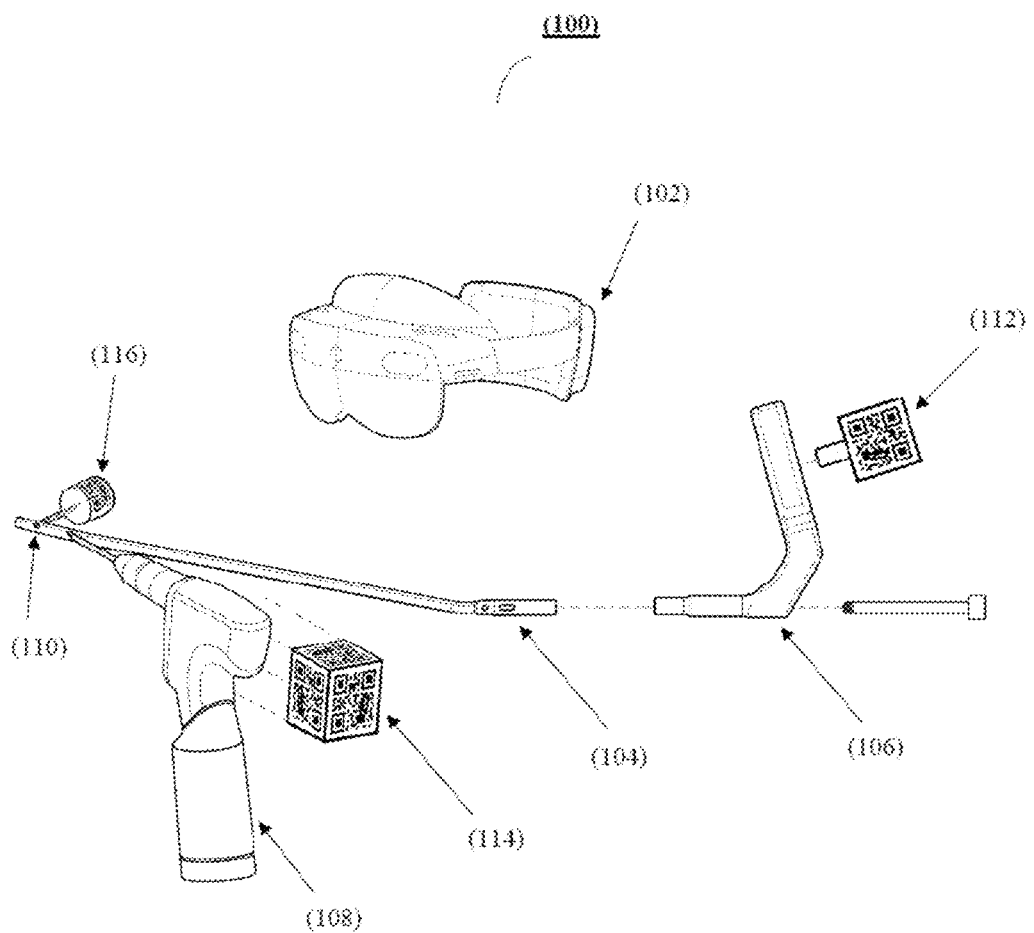

Referring now to FIGS. 1A and 1B, a system 100 for providing visual guidance in a medical surgery is illustrated, in accordance with an embodiment of the present subject matter. The system 100 herein is a distributed system configured in form of plurality of components.

In one embodiment, the system 100 may comprise the plurality of components such as a virtual assistance device 102 for providing visual guidance in a medical surgery. The virtual assistance device 102 may comprise a head mounted virtual assistance device such as a Microsoft HoloLens, Magic Leap 1 Lightwear. The virtual assistance device 102 may be used to create a mixed reality environment for performing the medical surgery.

The system 100 may further comprise a construct (assembly) of a physical medical implant having at least one of a physical Intra-Medullary (IM) nail implant 104 and a physical insertion handle 106. The physical insertion handle 106 may be attached to the physical IM nail implant 104, thereby forming the construct. A first QR code 112 may be provided on the physical insertion handle 106 for registering the construct within the virtual assistance device 102 by scanning the first QR code 112.

The system 100 may further comprise a physical drill gun 108 for performing one or more surgical steps. The one or more surgical steps may comprise one of a drilling into a bone selected as the target, a surgery of the bone. The physical drill gun 108 may be provided with a second QR code 114. The second QR code 114 may be provided for registering the physical drill gun 108 within the virtual assistance device 102.

Further, the one or more third QR codes 116 may be inserted into one or more hole(s) 110 provided over the physical IM nail implant 104. The one or more third QR codes 116 may be inserted temporarily and may be removed after the registration is completed. The one or more holes 110 may be provided for accepting screws during the medical surgery. In one embodiment, the one or more holes 110 may comprise a proximal lateral hole 1, proximal anterior hole 1 and 2, distal medial hole 1 and 2. The one or more holes may comprise a diameter of 4.1 mm (radius of 2.05 mm) and 1 oblong slot of 4.1×7 mm. The one or more third QR codes 116 may be provided for registering the coordinates of the one or more holes 110 with respect to the coordinates of the virtual impression of the physical IM nail implant 104 and the virtual impression of the physical insertion handle 106 within the virtual assistance device 102. The coordinates comprises Cartesian coordinates registering position of the virtual impression of the physical IM nail implant 104.

Figure 2:
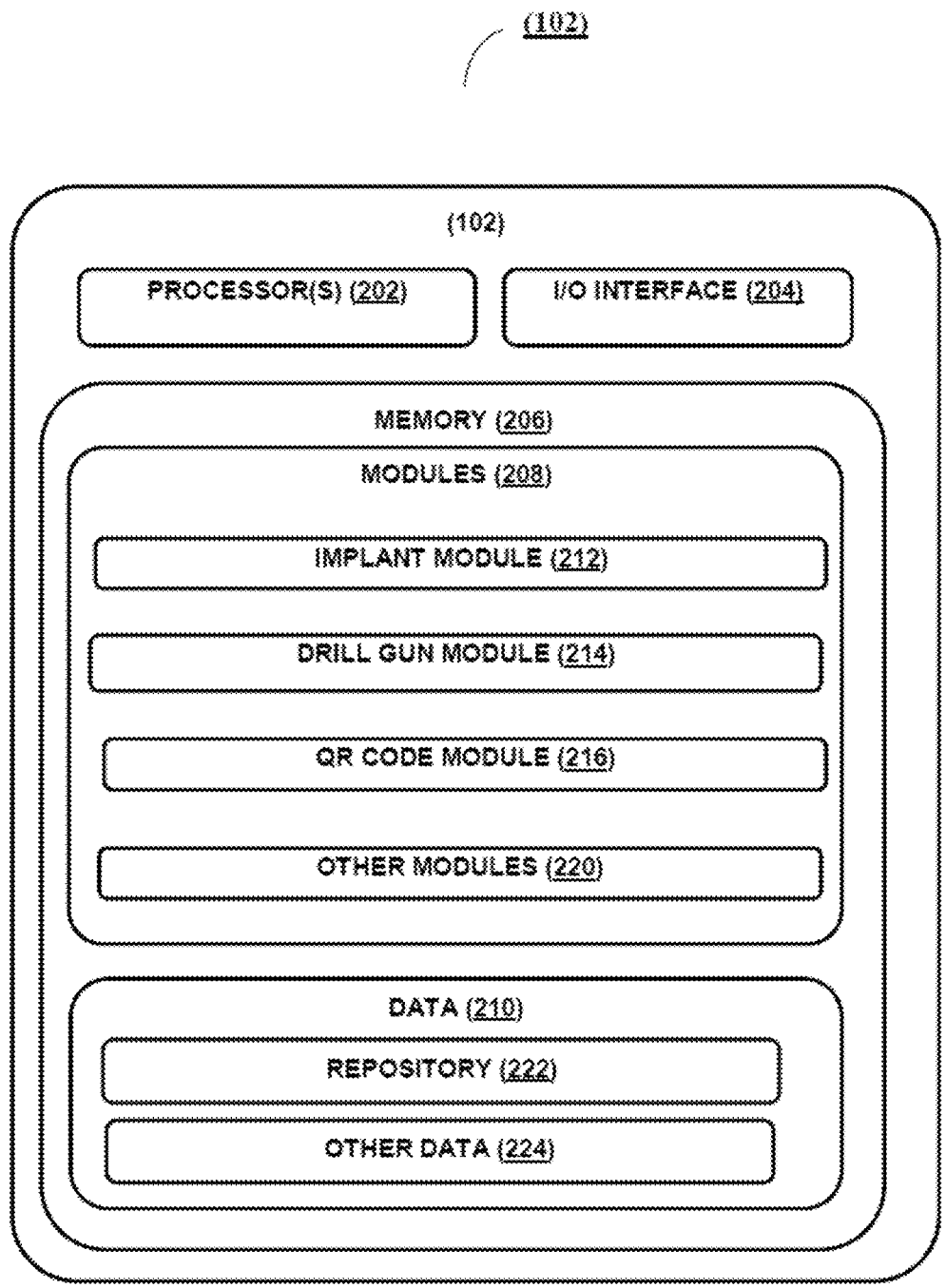
FIG. 2 illustrates a schematic diagram of a virtual assistance device 102 used in the system 100 for providing visual guidance in a medical surgery, in accordance with an embodiment of the present subject matter.

Referring now to FIG. 2, a virtual assistance device 102 used in the system 100 for providing visual guidance in a medical surgery, is illustrated in accordance with an embodiment of the present subject matter.

In one embodiment, the virtual assistance device 102 may include at least one processor 202, an input/output (I/O) interface/user interface 204, and a memory 206. The at least one processor 202 may be implemented as one or more microprocessors, microcomputers, microcontrollers, digital signal processors, central processing units, state machines, logic circuitries, and/or any devices that manipulate signals based on operational instructions. Among other capabilities, at least one processor 202 may be configured to fetch and execute computer-readable instructions stored in the memory 206.

The I/O interface 204 may include a variety of software and hardware interfaces, for example, a web interface, a graphical user interface, and the like. The I/O interface 204 may allow the virtual assistance device 102 to be also controlled or pre-configured through a user device. Further, the I/O interface 204 may enable the virtual assistance device 102 to communicate with other computing devices, such as web servers and external data servers (not shown). The I/O interface 204 may facilitate multiple communications within a wide variety of networks and protocol types, including wired networks, for example, LAN, cable, etc., and wireless networks, such as WLAN, cellular, or satellite. The I/O interface 204 may include one or more ports for connecting a number of devices to one another or to another server.

The memory 206 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. The memory 206 may include modules 208 and data 210.

The modules 208 may include routines, programs, objects, components, data structures, and the like, which perform particular tasks, functions or implement particular abstract data types. In one implementation, the modules 208 may include an implant module 212, a drill gun module 214, a QR code module 216, and other modules 220. The other modules 220 may include programs or coded instructions that supplement applications and functions of the virtual assistance device 102. The modules 208 described herein may be implemented as software modules that may be executed in the cloud-based computing environment of the virtual assistance device 102.

The data 210, amongst other things, serve as a repository for storing data processed, received, and generated by one or more of the modules 208. The data 210 may also include a repository 222, and other data 224. In one embodiment, the other data 224 may include data generated as a result of the execution of one or more modules in the other modules 220.

In one implementation, a user/medical practitioner may access the virtual assistance device 102 via the I/O interface 204. The user may be registered using the I/O interface 204 in order to use the virtual assistance device 102. In one aspect, the user may access the I/O interface 204 of the virtual assistance device 102 for obtaining information, providing input information or configuring the virtual assistance device 102.

In one embodiment, the virtual assistance device 102 may comprise an implant module 212 configured to create and store one or more virtual medical implant models as pre-stored data used in performing a medical surgery.

In one embodiment, the virtual assistance device 102 may comprise a drill gun module 214 configured to create and store one or more virtual drill gun models as pre-stored data, used in performing a medical surgery.

In one embodiment, the virtual assistance device 102 may comprise a QR code module 216 configured to pre-store information regarding QR code data used for scanning and mapping the QR codes for registration of one or more components used in a medical surgery. The one or more components comprises a physical IM nail implant 104 and a physical insertion handle 106, a physical drill gun 108. The QR code module 216 may also pre-store information regarding QR code data associated with one or more holes 110 provided on the physical IM nail implant 104.

Figure 3A:
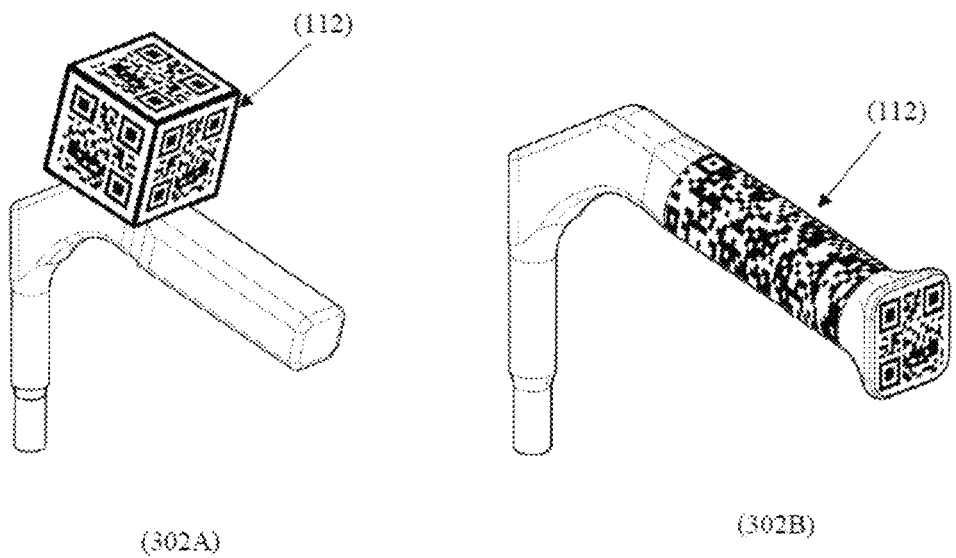
FIGS. 3A, 3B and 3C illustrate examples of one or more QR codes used in the system 100 for providing visual guidance in a medical surgery, in accordance with an embodiment of the present subject matter.
Figure 3B:
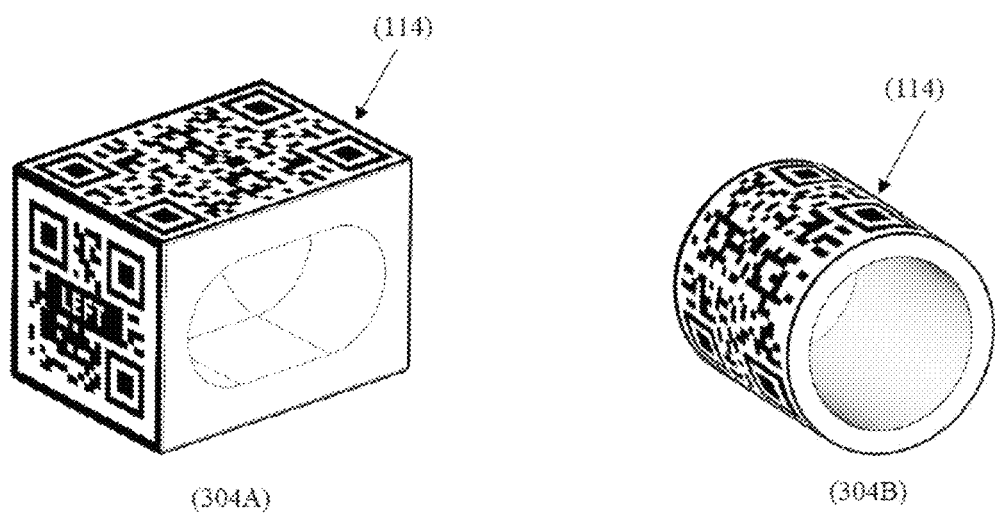
Figure 3C:
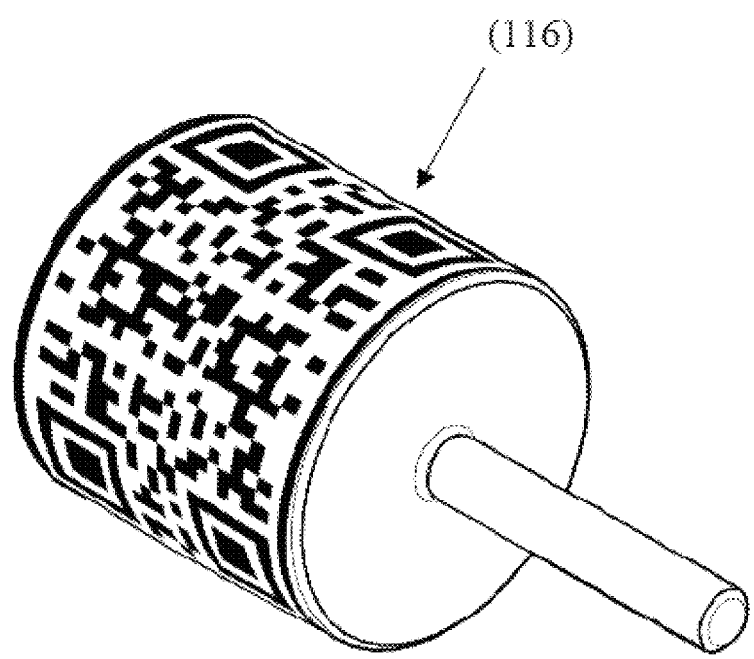

Referring now to FIGS. 3A, 3B and 3C, examples of the one or more QR codes used in the system 100 for providing visual guidance in a medical surgery are illustrated, in accordance with an embodiment of the present subject matter.

In one embodiment, the first QR code 112 may be provided on the physical insertion handle 106 as shown in FIG. 3A. In one aspect 302A, the first QR code 112 may be provided as a cubical QR code on the physical insertion handle 106. In another aspect 302B, the first QR code 112 may be provided as a QR code integrated on the physical insertion handle 106.

In one embodiment, the second QR code 114 may be provided on the physical drill gun 108 as shown in FIG. 3B. In one aspect 304A, the second cubical QR code 114 may be attached to the backend of the physical drill gun 108. In another aspect 304B, the second cylindrical QR code 114 may be attached to the physical drill gun chuck (stationary part) 108.

In one embodiment, the third QR code 116 may be inserted to the one or more holes 110 provided on the physical IM nail implant 104 as shown in FIG. 3C. The third QR code 116 may be a cylindrical QR code. The insertion of the third cylindrical QR code 116 is temporary and may be removed once the coordinates of the one or more holes 110 are registered.

Referring now to FIGS. 4A, 4B, 4C, 4D, 4E, 4F, and 4G, the user interface/I/O interface 204 used in the system 100 for providing visual guidance in a medical surgery is illustrated, in accordance with an embodiment of the present subject matter.

Figure 4A:
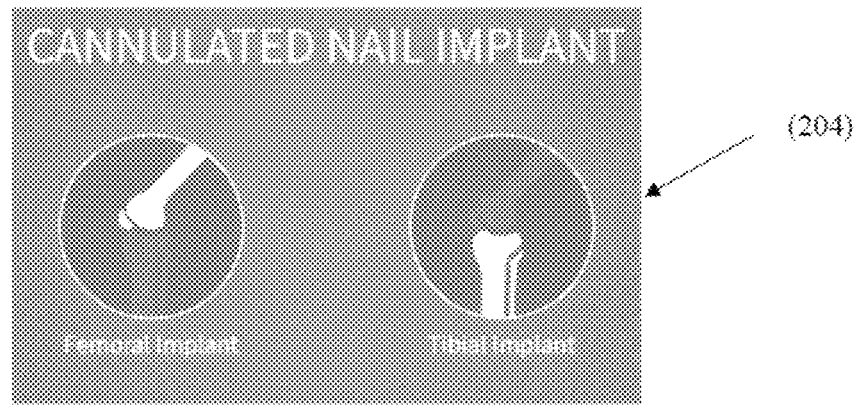
FIGS. 4A, 4B, 4C, 4D, 4E, 4F, and 4G illustrate a user interface 204 of the system 100 for providing visual guidance in a medical surgery, in accordance with an embodiment of the present subject matter.
Figure 4B:
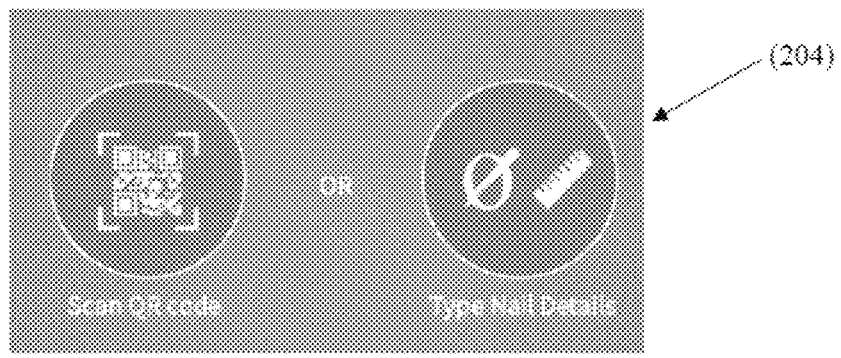
Figure 4C:
Figure 4D:
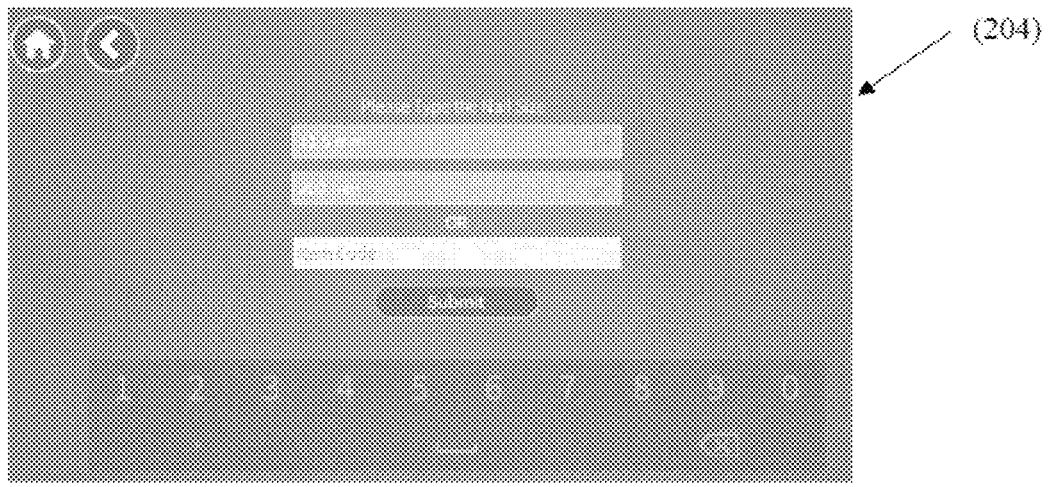
Figure 4E:
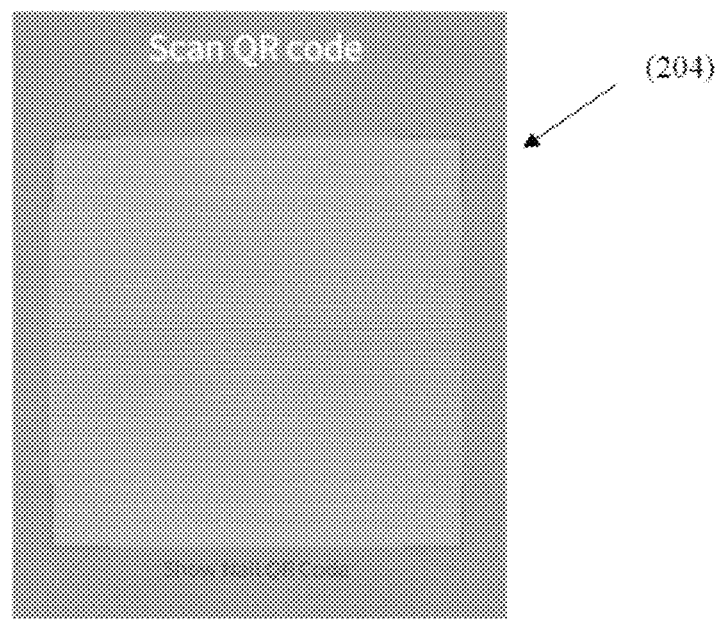
Figure 4F:
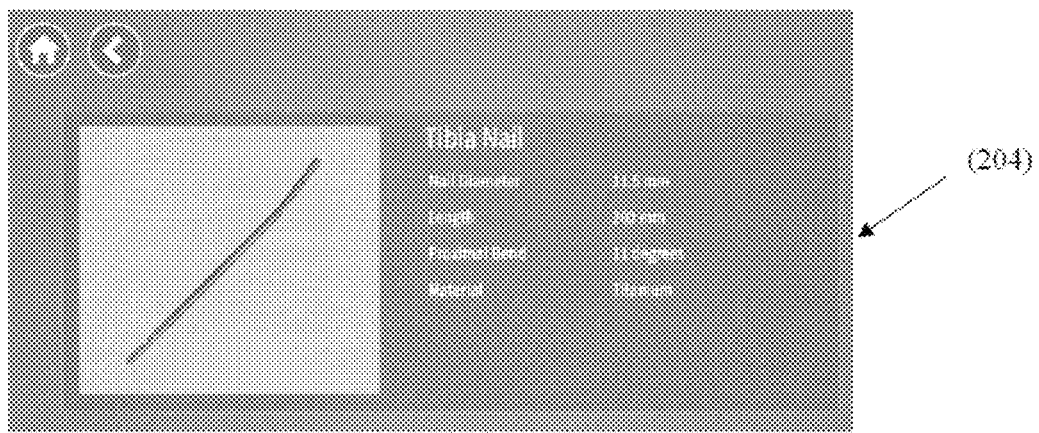
Figure 4G:
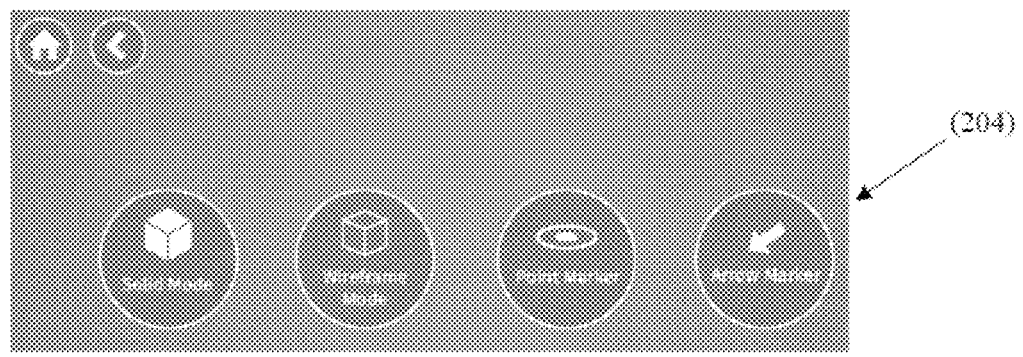

The user interface/I/O interface 204 is provided on the virtual assistance device 102 for interaction with the medical practitioner while performing the medical surgery. The medical practitioner may access the I/O interface 204 by entering login credentials. The I/O interface 204 may allow the medical practitioner to navigate through the I/O interface 204 to select one or more pre-stored nail implants as shown in FIG. 4A. Further, the user interface 204 may allow the medical practitioner to scan the one or more QR codes as shown in FIGS. 4B and 4E, type nail details as shown in FIGS. 4B, 4C, 4D, and 4F, and provide one or more commands through voice, gesture and likewise.

Referring now to FIGS. 5A, 5B, 5C, 5D, 5E, 5F, 5G, 5H, 5I, 5J and 5K, a method 500 for providing visual guidance in a medical surgery is illustrated, in accordance with an embodiment of the present subject matter.

The method 500 may be described in the general context of computer executable instructions. Generally, computer executable instructions can include routines, programs, objects, components, data structures, procedures, modules, functions, and the like, that perform particular functions or implement particular abstract data types. The method 500 may also be practiced in a distributed computing environment where functions are performed by remote processing devices that are linked through a communications network. In a distributed computing environment, computer executable instructions may be located in both local and remote computer storage media, including memory storage devices.

The order in which the method 500 is described is not intended to be construed as a limitation, and any number of the described method steps can be combined in any order to implement the method 500 or alternate methods. Additionally, individual steps may be deleted from the method 500 without departing from the spirit and scope of the subject matter described herein. Furthermore, the method 500 can be implemented in any suitable hardware, software, firmware, or combination thereof. However, for ease of explanation, in the embodiments described below, the method 500 may be considered to be implemented in the above described system 100.

Figure 5A:
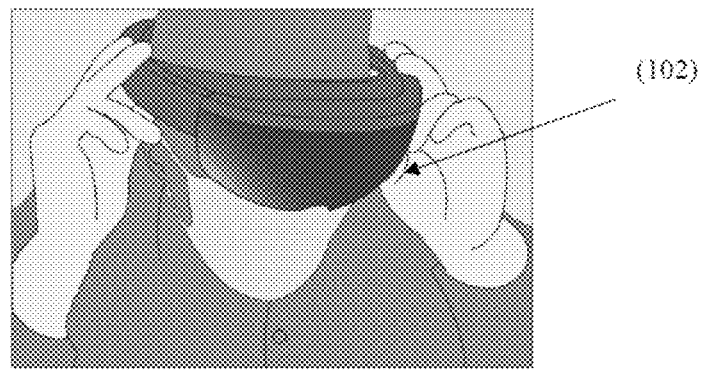
FIGS. 5A, 5B, 5C, 5D, 5E, 5F, 5G, 5H, SI, 5J and 5K illustrate a method 500 for providing visual guidance in a medical surgery, in accordance with an embodiment of the present subject matter.
Figure 5B:
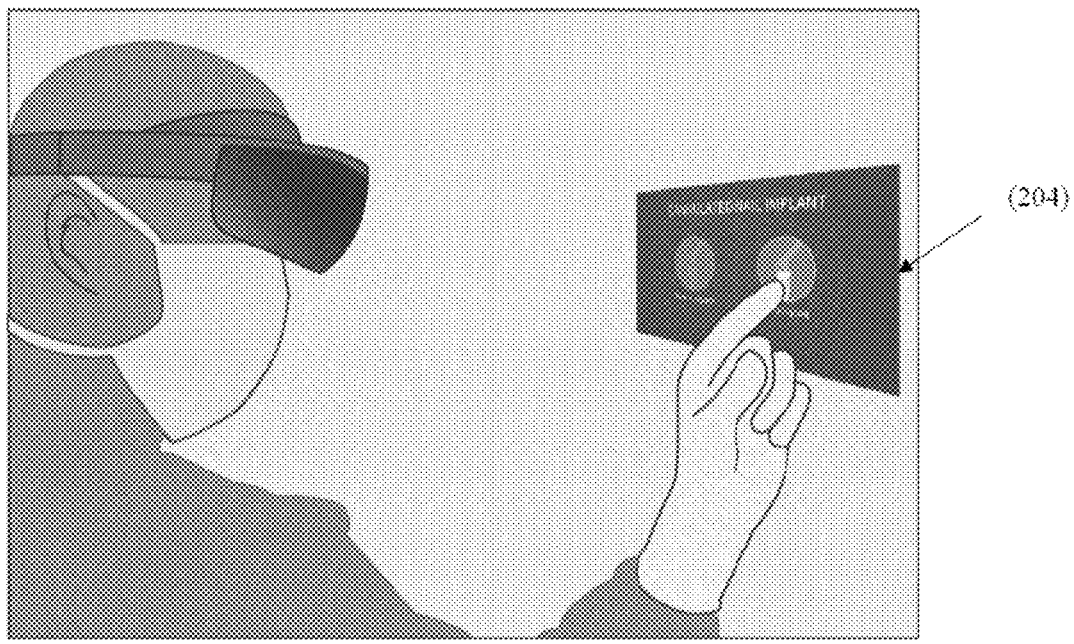
Figure 5C:
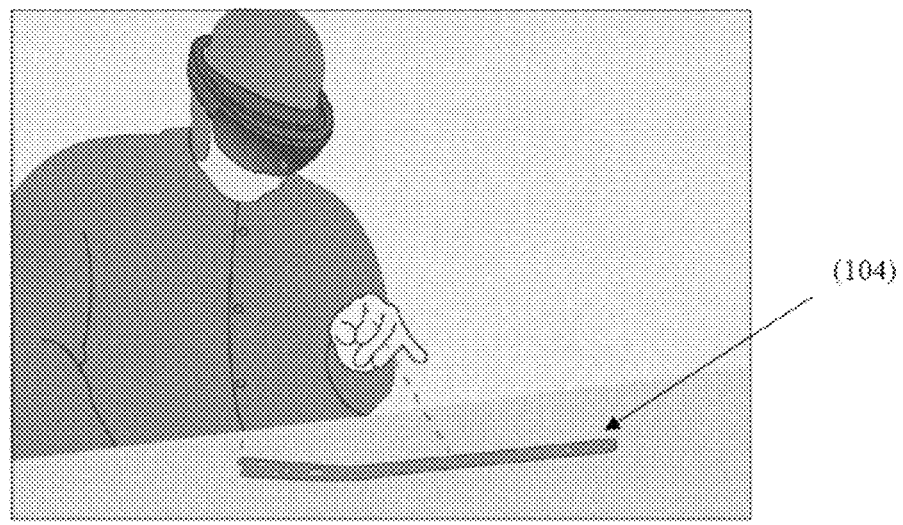

Initially the virtual assistance device 102 may be worn by a surgeon (medical practitioner) for performing a medical surgery as shown in FIG. 5A. The virtual assistance device 102 may comprise the head mounted virtual assistance device such as a Microsoft HoloLens. The virtual assistance device 102 may comprise the combination of the virtual medical implant, the Intra-Medullary (IM) nail model and the virtual insertion handle model stored in the implant module 212. The virtual medical implant may be selected by the medical practitioner by navigating through the user interface 204 as shown in FIG. 5B. Further, the physical IM nail implant 104 to be used in the medical surgery may be scanned by the medical practitioner as shown in FIG. 5C.

Figure 5D:
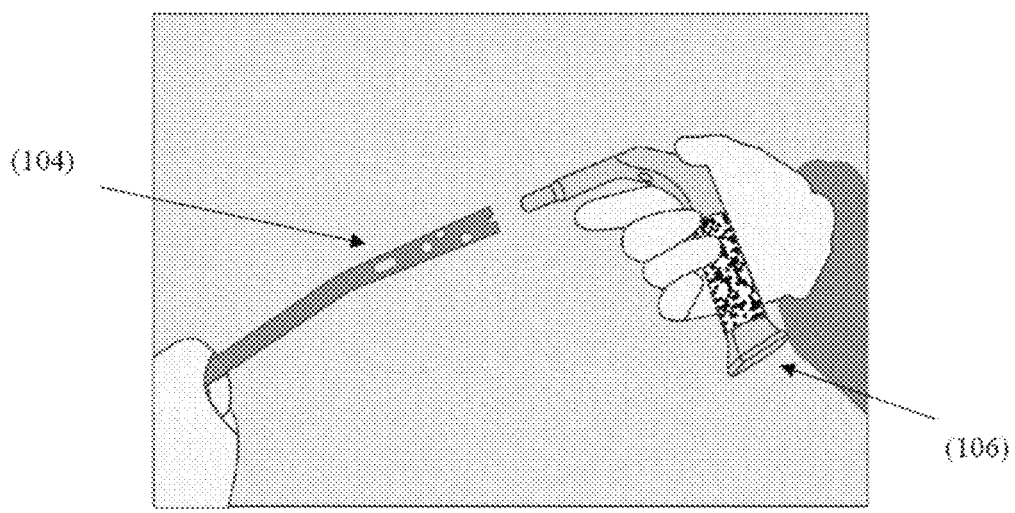
Figure 5E:
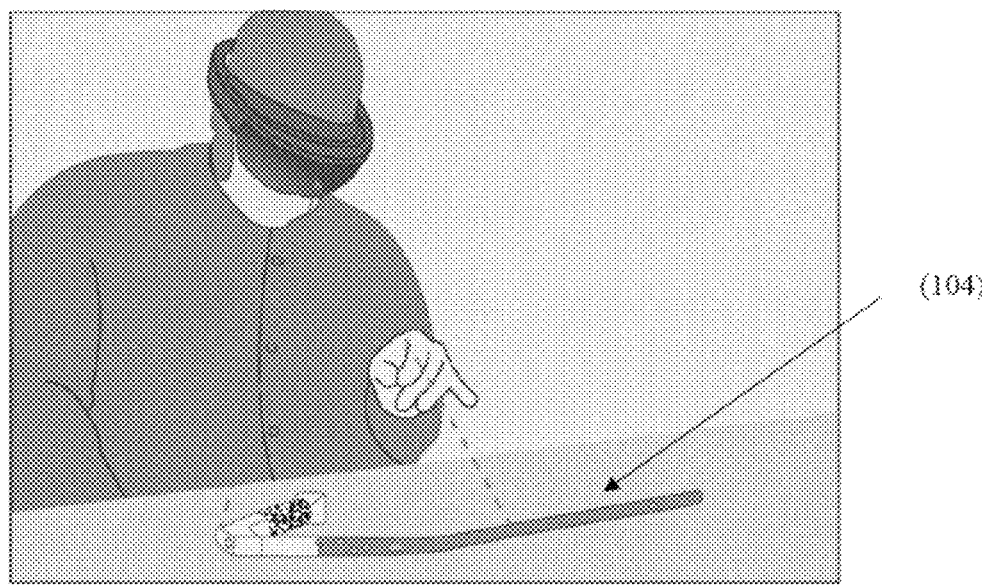

Further, the first QR code 112 may be attached to the physical insertion handle 106. The physical insertion handle 106 may be attached to the physical IM nail implant 104, thereby forming a construct (assembly) as shown in FIG. 5D. Furthermore, the first QR code 112 may be scanned to register the physical IM nail implant 104 along with the physical insertion handle 106 within the virtual assistance device 102 as shown in FIG. 5E. The first QR code 112 may be sensed by the virtual assistance device 102. The virtual IM nail model may create a virtual impression of the physical IM nail implant 104 within the virtual assistance device 102 using the implant module 212.

In one embodiment, the registering may comprise selecting, through the User Interface (UI) 204, a pre-stored virtual medical implant, the Intra-Medullary (IM) nail model and the virtual insertion handle model for creating the virtual impression of the physical IM nail 104 within the virtual assistance device 102 based on the registering. Once the first QR code 112 is scanned, the pre-stored QR data in the virtual assistance device 102 may show the pre-stored virtual medical implant to be selected for creating the virtual impression of the physical IM nail implant 104.

Figure 5F:
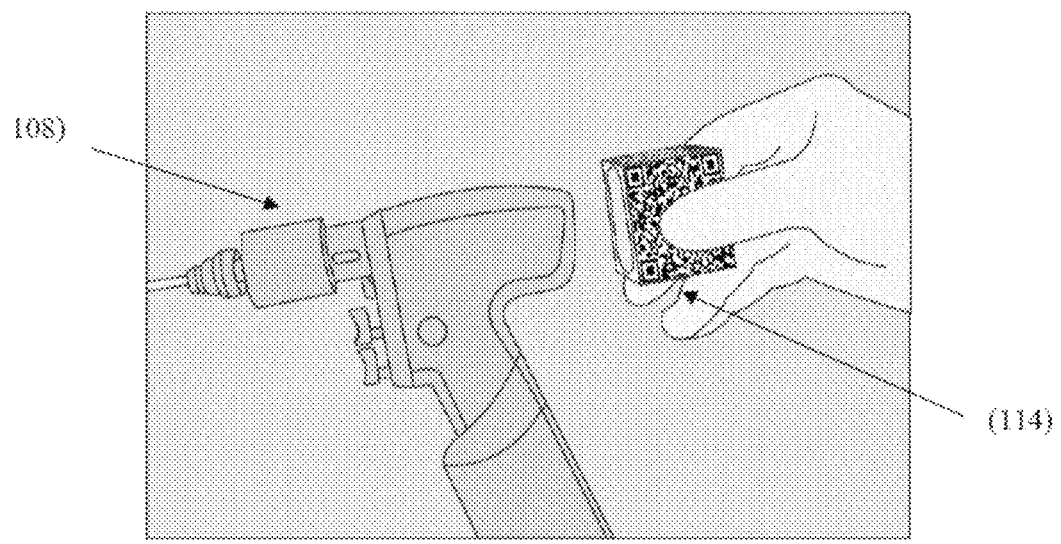

Further, the virtual assistance device 102 may comprise the virtual drill gun model stored in the drill gun module 214. The second QR code 114 may be attached to the physical drill gun 108 as shown in FIG. 5F. The physical drill gun 108 may be registered with the virtual assistance device 102 by scanning the second QR code 114 attached to the physical drill gun 108. Upon registration, the drill gun model may create a virtual impression of the physical drill gun 108 within the virtual assistance device 102. Once the second QR code 114 is scanned, the pre-stored QR code data in the virtual assistance device 102 may show the pre-stored drill gun model to be selected for creating the virtual impression of the physical drill gun 108.

Figure 5G:
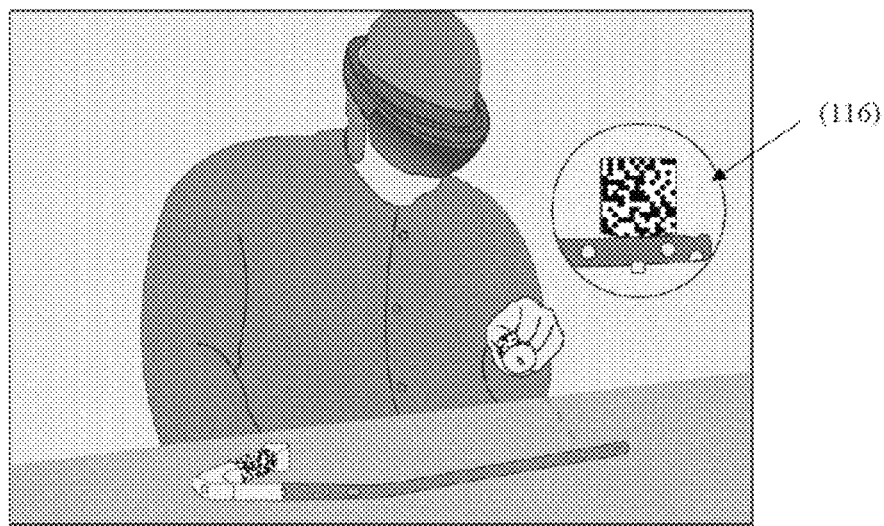

Further, one or more third QR codes 116 may be inserted into one or more hole(s) 110 provided over the physical IM nail implant 104 as shown in FIG. 5G. The one or more holes 110 may be provided for accepting screws during the medical surgery. The coordinates of the one or more holes 110 with respect to the coordinates of the virtual impression of the physical IM nail implant 104 and the physical insertion handle 106 may be registered within the virtual assistance device 102 by scanning the one or more third QR codes 116 as shown in FIG. 5G.

Figure 5H:
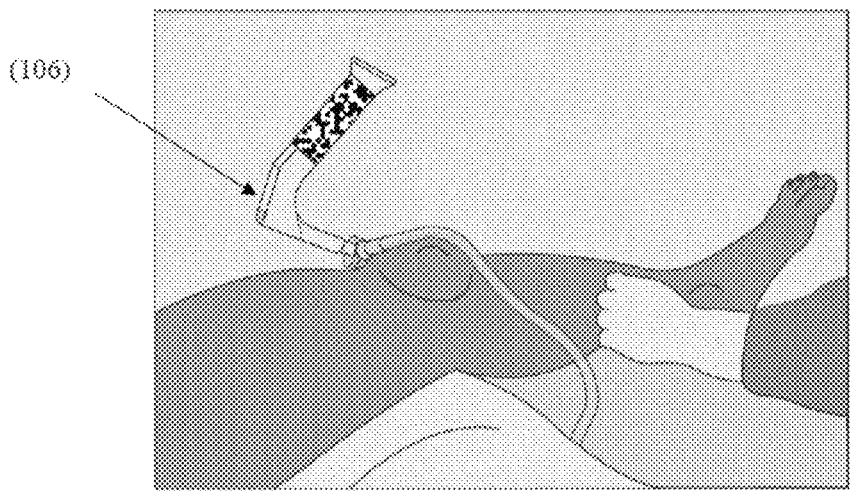

Upon registering, the physical IM nail implant 104 along with the insertion handle 106 may be inserted into a target as shown in FIG. 5H. The target may indicate an area inside an IM canal of the bone within the human body.

Figure 5I:
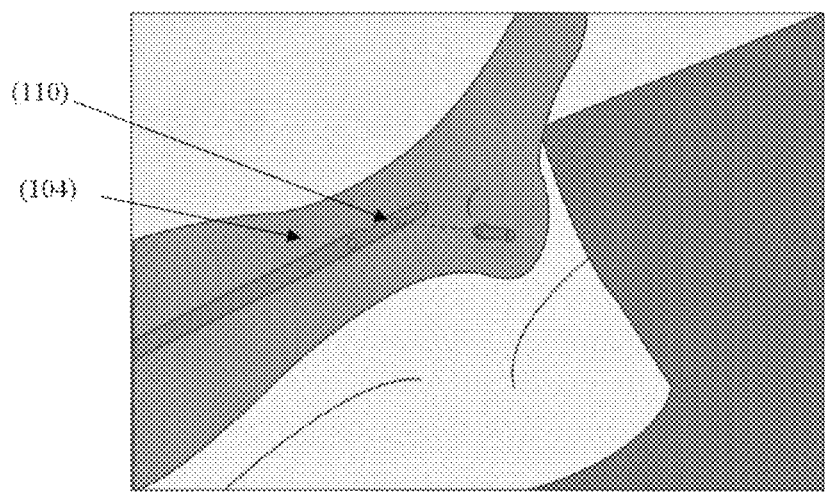

Further, each of the virtual impression of the physical IM nail implant 104 inside the target, the virtual impression of the physical drill gun 108, and the coordinates of the one or more holes 110 may be displayed, over the virtual assistance device 102 as shown in FIG. 5I. Further, the virtual impression of the physical drill gun 108 may be positioned over the virtual impression of the physical IM nail implant 104 inside the target as shown in FIG. 5J.

Figure 5J:
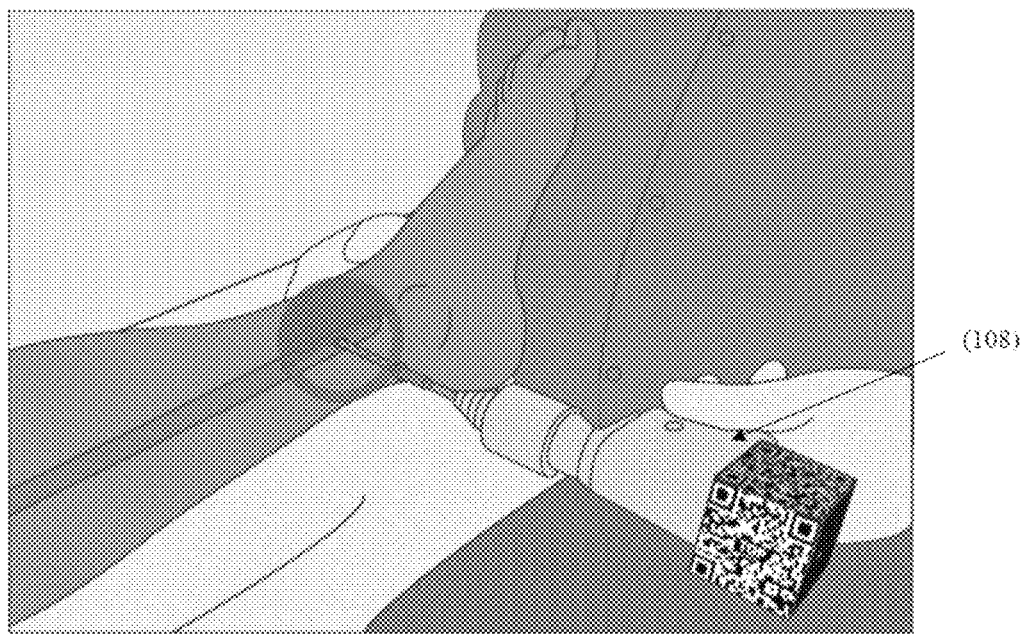
Figure 5K:
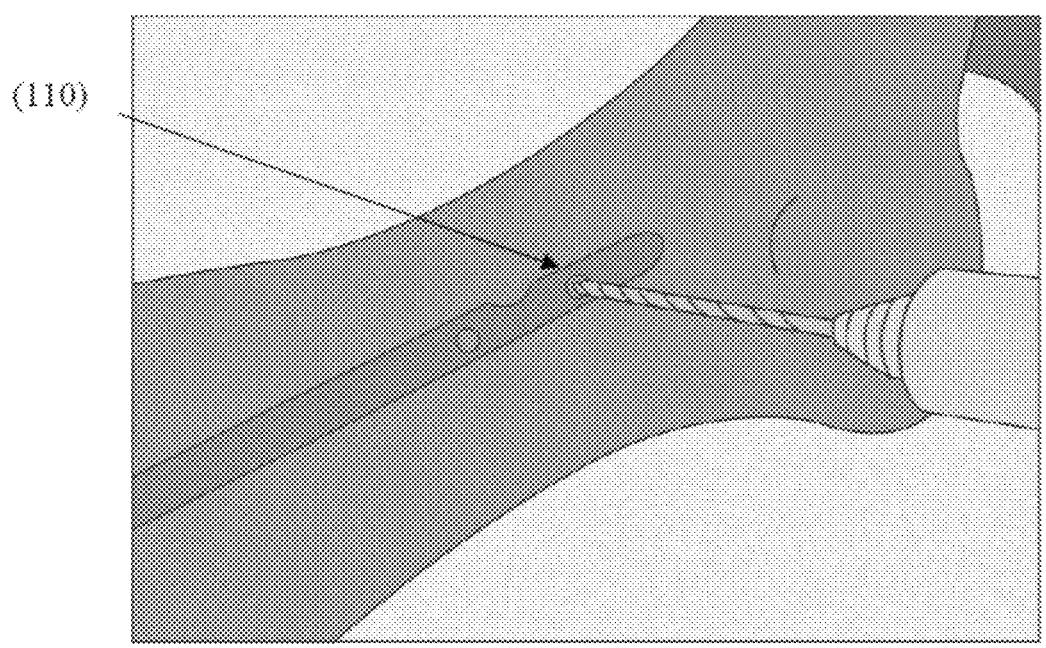

Further, the virtual impression of a drill tip of the physical drill gun 108 may be aligned over the one or more holes 110 through guidance of the coordinates of the one or more holes 110 registered within the virtual assistance device 102 as shown in FIG. 5J. The aligning may guide movement of the physical drill gun 108 over the target in real-time. In addition, the aligning may provide a positional and angular alignment of the virtual impression of a drill axis of the physical drill gun 108 over the co-ordinates of the one or more holes 110 in real-time. Furthermore, one or more surgical steps may be performed through the physical drill gun 108 over the target based on the aligning as shown in FIG. 5K. The one or more surgical steps may comprise one of a drilling into a bone selected as the target, a surgery of the bone.

In one embodiment, the virtual assistance device 102 may be configured to receive a voice command from a medical practitioner for selecting a hole from the one or more holes 110 for drilling. The selecting may be performed based on the aligning of the virtual impression of the physical drill gun 108 over the one or more holes 110. The voice command may be received through the processor 202 of the system 100, and may help to avoid confusion as to which hole from the one or more holes 110, the drill gun 108 is close to, as in some scenario the drill tip of the drill gun 108 may end up showing positional indicators with multiple holes.

In one embodiment, the virtual assistance device 102 may be also configured to generate one or more alerts regarding miscoordination in the one or more medical steps. The miscoordination comprises improper positioning and angular alignment of the physical drill gun 108 over the one or more holes 110 in real time. The one or more alerts such as visual or voice-based commands may be generated for a medical practitioner while performing the one or more medical steps, in order to ensure collinearity of the drill axis of the physical drill gun 108 with the co-ordinates of the one or more holes 110.

Referring now to FIGS. 6A, 6B, 6C, 6D, and 6E, exemplary embodiments of the method 500 for providing visual guidance in a medical surgery are illustrated, in accordance with an embodiment of the present subject matter.

Figure 6A:
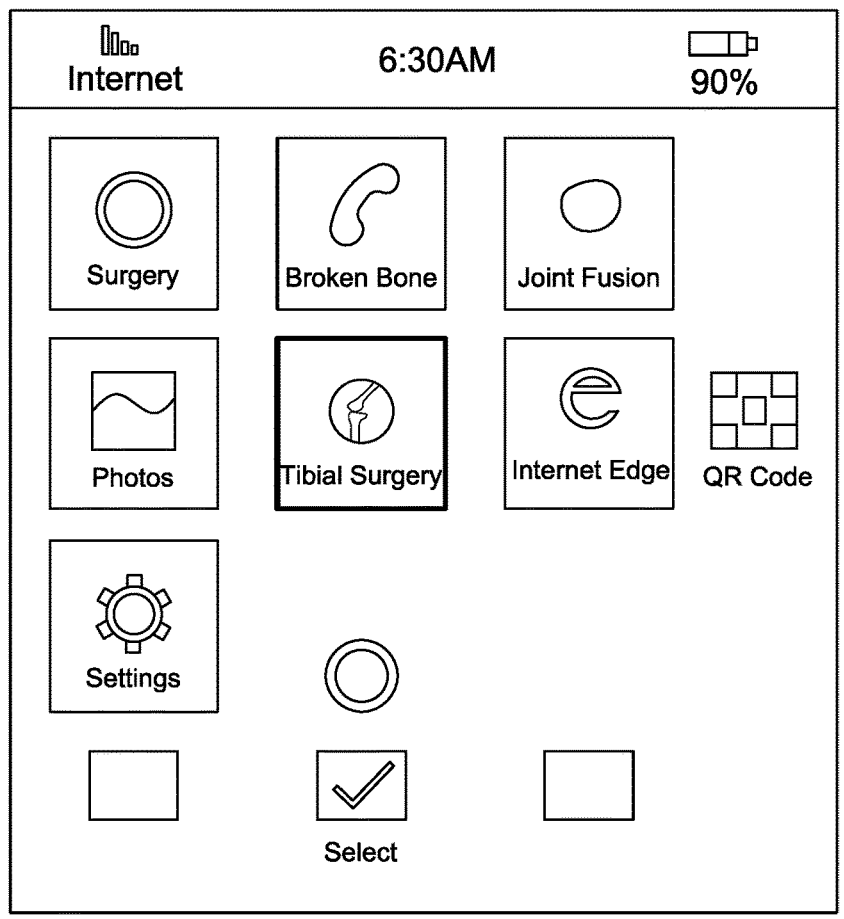
FIGS. 6A, 6B, 6C, 6D, 6E, 6F, 6G, 6H, and 6I illustrate exemplary embodiments of the method 500 for providing visual guidance in a medical surgery, in accordance with an embodiment of the present subject matter.
Figure 6B:
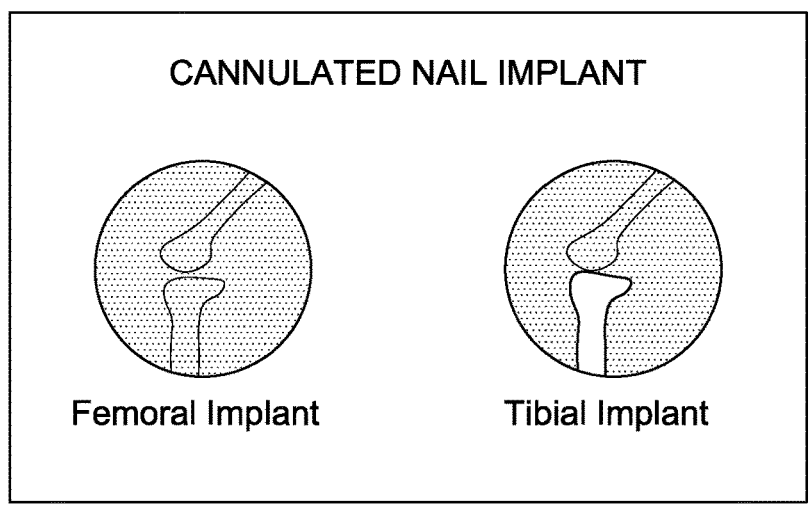

In one embodiment, FIG. 6A shows a mixed reality application. Further, selection of a virtual implant model from the one or more virtual implant models stored within the virtual assistance device 102 may be performed. For example, a cannulated nail implant mode may be selected from the one or more virtual implant models as shown in FIG. 6B.

Figure 6C:
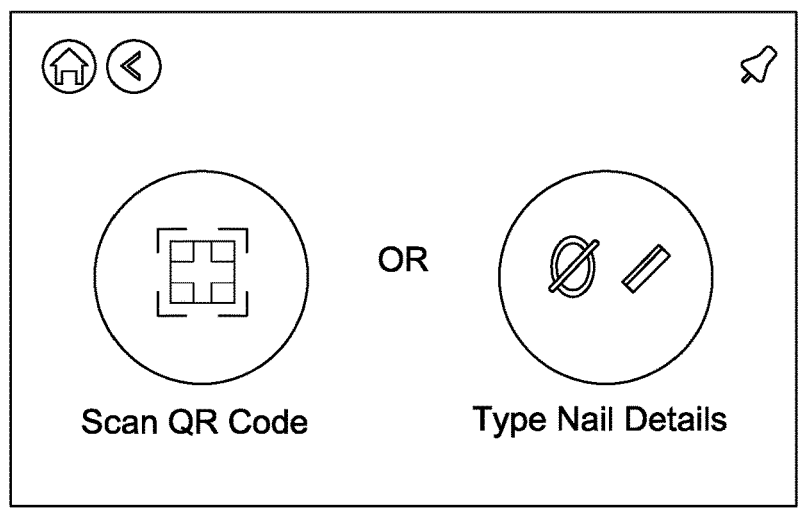
Figure 6D:
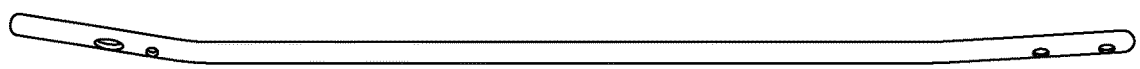

In one embodiment, a size of the medical implant may be selected as shown in FIG. 6C. Further, FIG. 6D shows a physical IM nail implant 104 of the medical implant with a QR code attachment. The physical IM nail implant 104 may be attached with the physical insertion handle 106, thereby forming a construct (assembly).

Figure 6E:
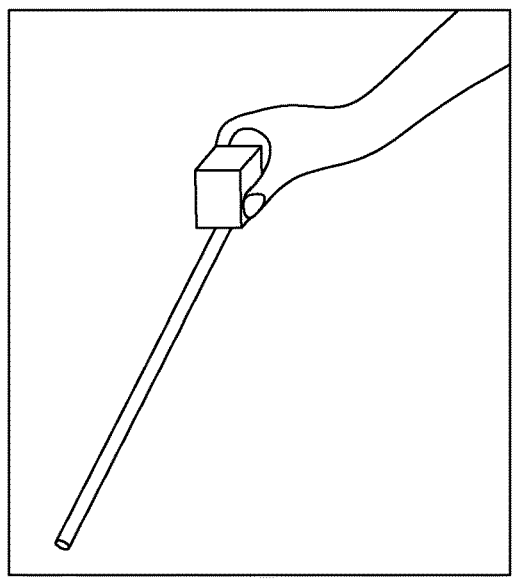

Further, a calibration of one or more holes 110 provided on the physical IM nail implant 104 may be performed with the help of the QR code module 216, as shown in FIG. 6E. The calibration of the one or more holes 110 may be performed to register axis of the one or more holes 110 for improving an accuracy of positioning and angular alignment of the tip of the physical drill gun 108 over the one or more holes 110. Further, the method 500 provides a negating effect on tolerance of the physical IM nail implant 104.

Figure 6F:
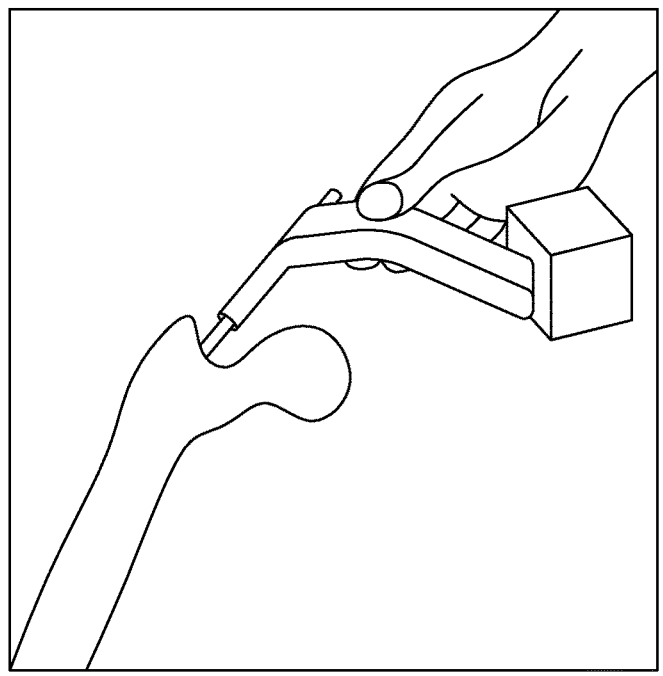

In one embodiment, the physical IM nail implant 104 along with the physical insertion handle 106 may be inserted inside a target such as an area inside an IM canal of the bone within the human body bone, as shown in FIG. 6F.

Figure 6G:
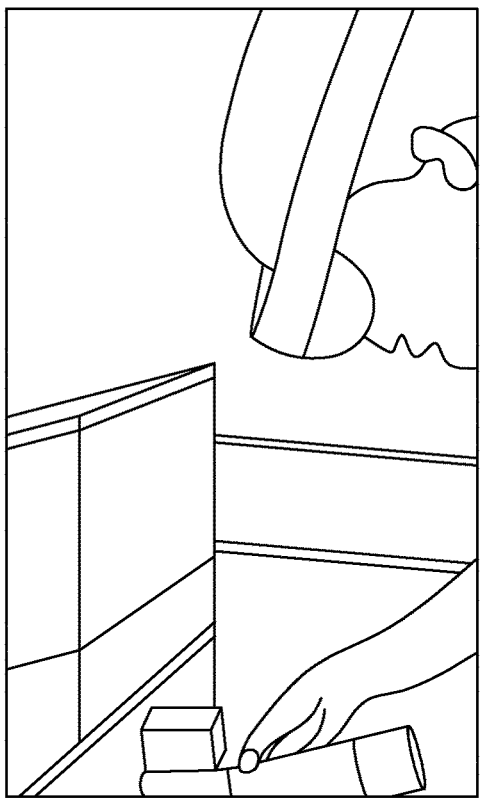

Furthermore, a drill axis of the drill gun 108 with the second QR code 114 may be aligned over the registered co-ordinates of the one or more holes 110 as shown in FIG. 6G.

Figure 6H:
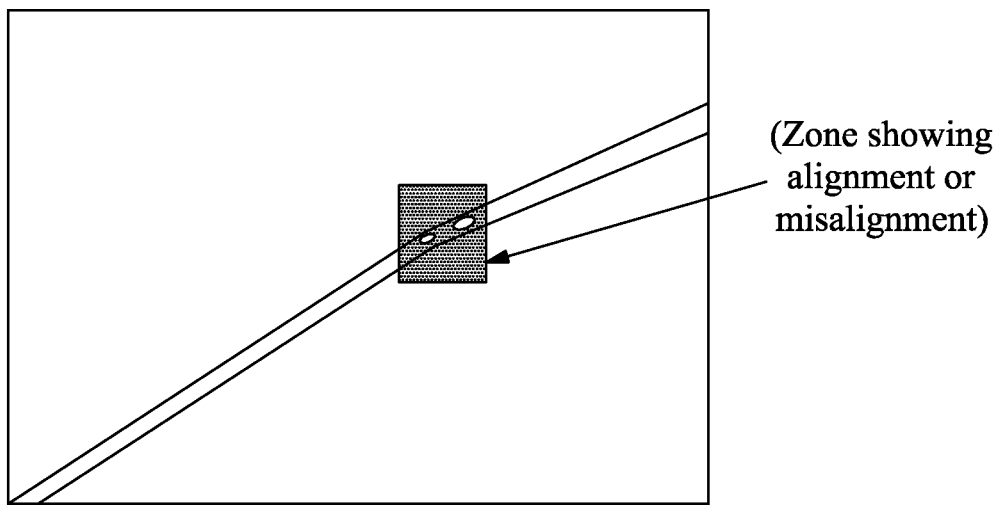

In one embodiment, the FIG. 6H shows a virtual impression of the physical IM nail implant 104 inside the target, the virtual impression of the physical drill gun 108, and the coordinates of the one or more holes 110 displayed over the virtual assistance device 102. The virtual hologram is now projected on the real-time view of the target on a patient's body through the virtual assistance device 102 with positional and angular alignment. The FIG. 6H also illustrates a zone showing alignment or misalignment. Further, one or more visual alerts in the form of one or more colours and graphical pointers, are displayed with additional auditory feedback to ensure collinearity of the drill axis of the physical drill gun 108 with the co-ordinates of the one or more holes 110.

Figure 6I:
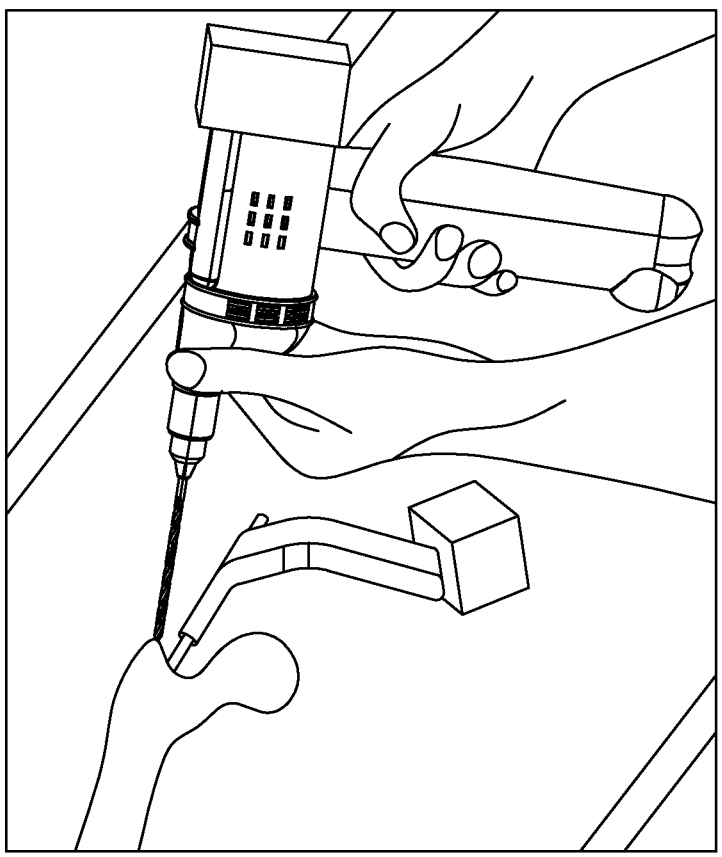

Further, based on the aligning and collinearity, one or more surgical steps such as drilling holes on the target through visual guidance may be performed as shown in FIG. 6I.

Figure 7:
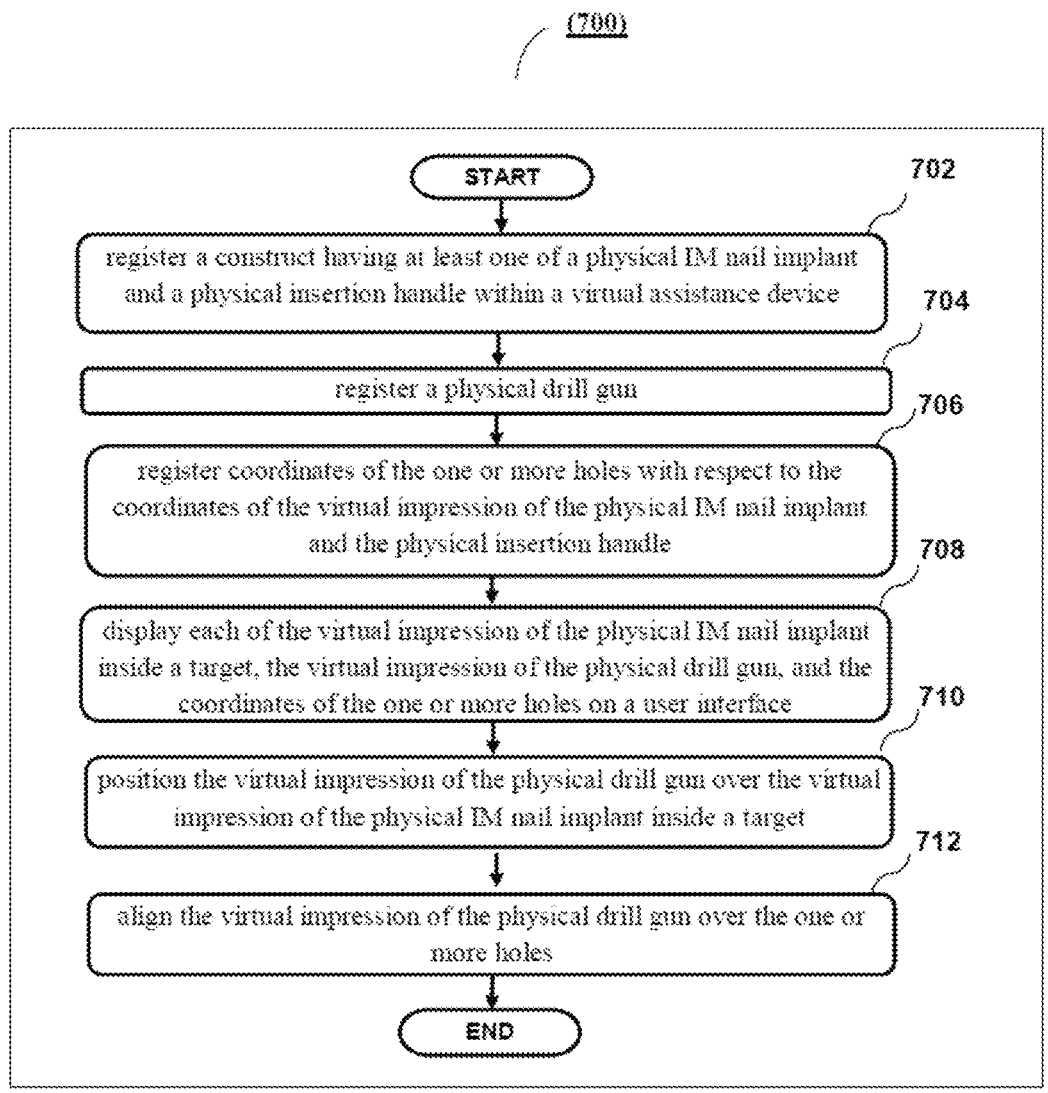
FIG. 7 illustrates a method 700 for providing visual guidance in a medical surgery, in accordance with an embodiment of the present subject matter.

Referring now to FIG. 7, a method 700 for providing visual guidance in a medical surgery is illustrated, in accordance with an embodiment of the present subject matter.

The method 700 may be described in the general context of computer executable instructions. Generally, computer executable instructions can include routines, programs, objects, components, data structures, procedures, modules, functions, and the like, that perform particular functions or implement particular abstract data types. The method 700 may also be practiced in a distributed computing environment where functions are performed by remote processing devices that are linked through a communications network. In a distributed computing environment, computer executable instructions may be located in both local and remote computer storage media, including memory storage devices.

The order in which the method 700 is described is not intended to be construed as a limitation, and any number of the described method steps can be combined in any order to implement the method 700 or alternate methods. Additionally, individual steps may be deleted from the method 700 without departing from the spirit and scope of the subject matter described herein. Furthermore, the method 700 can be implemented in any suitable hardware, software, firmware, or combination thereof. However, for ease of explanation, in the embodiments described below, the method 700 may be considered to be implemented in the above described virtual assistance device 102.

At block 702, a construct having at least one of a physical IM nail implant 104 and a physical insertion handle 106 may be registered, by a processor 202 within a virtual assistance device 102. Further, the registering may comprise scanning a first QR code 112 attached to the physical insertion handle 106. The first QR code 112 may be sensed by the virtual assistance device 102. Further, a virtual IM nail model may create a virtual impression of the physical IM nail implant 104 and the physical insertion handle 106 within the virtual assistance device 102.

At block 704, a physical drill gun 108 may be registered by the processor 202. The registering of the physical drill gun 108 may comprise scanning a second QR code 114 attached to the physical drill gun 108. A drill gun model may create a virtual impression of the physical drill gun 108 within the virtual assistance device 102.

At block 706, coordinates of the one or more holes 110 provided over the physical IM nail implant 104 for accepting screws during the medical surgery may be registered by the processor with respect to the coordinates of the virtual impression of the physical IM nail implant 104 and the physical insertion handle 106, through one or more third QR codes 116 inserted on the one or more holes 110.

At block 708, each of the virtual impression of the physical IM nail implant 104 inside a target, the virtual impression of the physical drill gun 108, and the coordinates of the one or more holes 110 may be displayed on a user interface 204, while inserting, each of the physical IM nail implant 104 and the physical insertion handle 106 into the target.

At block 710, the virtual impression of the physical drill gun 108 may be positioned by the processor 202, over the virtual impression of the physical IM nail implant 104 inside a target.

At block 712, the virtual impression of the physical drill gun 108 may be aligned by the processor 202, over the one or more holes 110 based on the coordinates of the one or more holes 110 registered within the virtual assistance device 102. The aligning may guide movement of the physical drill gun 108 over the target in real-time while performing one or more surgical steps over the target through the physical drill gun 108.

Exemplary embodiments discussed above may provide certain advantages. Though not required to practice aspects of the disclosure, these advantages may include those provided by the following features.

Some embodiments of the system and the method improve the surgical procedure by providing visual guidance.

Some embodiments of the system and the method eliminate the multiple X-ray scanning procedure and trial and error based method.

Some embodiments of the system and the method reduce the cost of the surgery, time consumption, and health risk associated with the patient due to elimination of multiple X-ray scanning procedure and trial and error based method.

Some embodiments of the system and the method may provide life size augmented virtual models for seamless user experience to the medical practitioner.

Some embodiments of the system and the method reduce dependency on the medical practitioner's skills and visual judgment, thereby increasing efficiency of the surgical procedure.

Some embodiments of the system and the method generate visual or auditory alerts for the medical practitioner while performing a medical surgery.

Some embodiments of the system and the method improve the positional and angular accuracy over conventional system by taking the surgeon's aid to calibrate the positions of the screw holes on the IM nail implant with the help of the QR code. The precision tolerance requirement on the screw holes, which are long apart (for example 300 to 400 mm), is drastically reduced.

Some embodiments of the system and the method reduce an overall manufacturing cost of the IM nail implant, by eliminating the need for precise manufacturing of the screw holes on the IM nail implant to achieve tight tolerances for positional and angular accuracy.

Although implementations for system and method for providing visual guidance in a medical surgery, it is to be understood that the appended claims are not necessarily limited to the specific features or methods described. Rather, the specific features and methods are disclosed as examples of implementations for providing visual guidance in a medical surgery.

The invention claimed is:

1. A method for providing visual guidance in a medical surgery, the method comprising:
    registering, within a virtual assistance device having a combination of a virtual medical implant, an Intra-Medullary (IM) nail model and a virtual insertion handle model, a construct having at least one of a physical IM nail implant and a physical insertion handle, wherein the registering is performed by scanning a first QR code attached to the physical insertion handle, and wherein the first QR code is sensed by the virtual assistance device, and wherein the virtual IM nail model creates a virtual impression of the physical IM nail implant and the physical insertion handle within the virtual assistance device;
    registering, within the virtual assistance device having a drill gun model, a physical drill gun by scanning a second QR code attached to the physical drill gun, wherein the drill gun model creates a virtual impression of the physical drill gun within the virtual assistance device;
    inserting, one or more third QR codes into one or more hole(s) provided over the physical IM nail implant, wherein the one or more holes are provided for accepting screws during the medical surgery;
    registering through the one or more third QR codes, within the virtual assistance device, coordinates of the one or more holes with respect to the coordinates of the virtual impression of the physical IM nail implant and the physical insertion handle;
    inserting, each of the physical IM nail implant and the physical insertion handle into a target;
    displaying, over the virtual assistance device, each of the virtual impression of the physical IM nail implant inside the target, the virtual impression of the physical drill gun, and the coordinates of the one or more holes;
    positioning, the virtual impression of the physical drill gun over the virtual impression of the physical IM nail implant inside the target;
    aligning, the virtual impression of the physical drill gun over the one or more holes based on the coordinates of the one or more holes registered within the virtual assistance device, wherein the aligning, guides movement of the physical drill gun over the target in real-time;
    performing, through the physical drill gun, one or more surgical steps over the target based on the aligning.

2. The method as claimed in claim 1, wherein the target indicates an area inside an IM canal of the bone within the human body.

3. The method as claimed in claim 1, wherein the one or more surgical steps comprise one of a drilling into a bone selected as the target, a surgery of the bone.

4. The method as claimed in claim 1, wherein the aligning provides a positional and angular alignment of the virtual impression of the physical drill gun over the one or more holes in real time.

5. The method as claimed in claim 1, wherein the virtual assistance device comprises a head mounted virtual assistance device, wherein the head mounted virtual assistance device comprises a HoloLens, Magic Leap 1 lightware.

6. The method as claimed in claim 1, wherein the registering comprises: selecting, through a User Interface (UI), a pre-stored virtual medical implant, an Intra-Medullary (IM) nail model and a virtual insertion handle model for creating the virtual impression of the physical IM nail implant within the virtual assistance device based on the registering.

7. The method as claimed in claim 1, comprises generating, through the virtual assistance device, one or more alerts regarding miscoordination in the one or more medical steps, wherein the miscoordination comprises improper positioning and angular alignment of the physical drill gun over the one or more holes in real time, and wherein the one or more alerts comprise one of a visual alert, an auditory alert.

8. The method as claimed in claim 1, comprises receiving, through the virtual assistance device, one or more voice commands from a medical practitioner for selecting a hole from the one or more holes for performing the one or more medical steps, wherein the selection is performed based on the aligning of the virtual impression of the physical drill gun over the one or more holes.

9. A system for providing visual guidance in a medical surgery, the system comprising:
    a virtual assistance device having a combination of a virtual medical implant, an Intra-Medullary (IM) nail model and a virtual insertion handle model, the virtual assistance device configured for:
registering, within the virtual assistance device, a construct having at least one of a physical IM nail implant and a physical insertion handle, wherein the registering is performed by scanning a first QR code attached to the physical insertion handle, and wherein the first QR code is sensed by the virtual assistance device, and wherein the virtual IM nail model creates a virtual impression of the physical IM nail implant and the physical insertion handle within the virtual assistance device;
registering, within the virtual assistance device having a drill gun model, a physical drill gun by scanning a second QR code attached to the physical drill gun, wherein the drill gun model creates a virtual impression of the physical drill gun within the virtual assistance device;
registering within the virtual assistance device, through one or more third QR codes inserted on one or more holes, coordinates of one or more holes with respect to the coordinates of the virtual impression of the physical IM nail implant and the physical insertion handle, wherein the one or more hole(s) are provided over the physical IM nail implant for accepting screws during the medical surgery;
displaying, over the virtual assistance device, each of the virtual impression of the physical IM nail implant inside a target, the virtual impression of the physical drill gun, and the coordinates of the one or more holes while inserting, each of the physical IM nail implant and the physical insertion handle into the target;
positioning, the virtual impression of the physical drill gun over the virtual impression of the physical IM nail implant inside the target;
aligning, the virtual impression of the physical drill gun over the one or more holes based on the coordinates of the one or more holes registered within the virtual assistance device, wherein the aligning guides movement of the physical drill gun over the target in real-time while performing one or more surgical steps over the target through the physical drill gun.

10. The system as claimed in claim 9, wherein the target indicates an area inside an IM canal of the bone within the human body.

11. The system as claimed in claim 9, wherein the one or more surgical steps comprise one of a drilling into a bone selected as the target, a surgery of the bone.

12. The system as claimed in claim 9, wherein the aligning provides a positional and angular alignment of the virtual impression of the physical drill gun over the one or more holes in real time.

13. The system as claimed in claim 9, wherein the virtual assistance device comprises a head mounted virtual assistance device, wherein the head mounted virtual assistance device comprises a HoloLens, Magic Leap 1 lightware.

14. The system as claimed in claim 9, wherein the virtual assistance device is configured for:
selecting, through a User Interface (UI), a pre-stored virtual medical implant, an Intra-Medullary (IM) nail model and a virtual insertion handle model for creating the virtual impression of the physical IM nail implant within the virtual assistance device based on the registering.

15. The system as claimed in claim 9, wherein the virtual assistance device generates one or more alerts regarding miscoordination in the one or more medical steps, wherein the miscoordination comprises improper positioning and angular alignment of the physical drill gun over the one or more holes in real time, and wherein the one or more alerts comprise one of a visual alert, auditory alert.

16. The system as claimed in claim 9, wherein the virtual assistance device is configured to:
receive, one or more voice commands from a medical practitioner for selecting a hole from the one or more holes for performing the one or more medical steps, wherein the selection is performed based on the aligning of the virtual impression of the physical drill gun over the one or more holes.

17. A virtual assistance device for providing visual guidance in a medical surgery, the virtual assistance device comprising:
a memory storing each of an Intra-Medullary (IM) nail model, a virtual insertion handle model, and a drill gun model;
a processor configured to execute a set of instructions stored in the memory, wherein the processor is configured for:
registering, a construct having at least one of a physical IM nail implant and a physical insertion handle, wherein the registering comprising:
scanning a first QR code attached to the physical insertion handle, and wherein the first QR code is sensed by in the virtual assistance device, and wherein the virtual IM nail model creates a virtual impression of the physical IM nail implant and the physical insertion handle within the virtual assistance device;
registering, a physical drill gun, the registering comprising:
scanning a second QR code attached to the physical drill gun, wherein the drill gun model creates a virtual impression of the physical drill gun within the virtual assistance device;
registering, through one or more third QR codes inserted on one or more holes provided over the physical IM nail implant for accepting screws during the medical surgery, coordinates of the one or more holes with respect to the coordinates of the virtual impression of the physical IM nail implant and the physical insertion handle;
a user interface configured for:
displaying, each of the virtual impression of the physical IM nail implant inside a target, the virtual impression of the physical drill gun, and the coordinates of the one or more holes while inserting, each of the physical IM nail implant and the physical insertion handle into the target; and wherein the processor is configured for:
positioning, the virtual impression of the physical drill gun over the virtual impression of the physical IM nail implant inside the target; and
aligning, the virtual impression of the physical drill gun over the one or more holes based on the coordinates of the one or more holes registered within the virtual assistance device, wherein the aligning guides movement of the physical drill gun over the target in real-time while performing one or more surgical steps over the target through the physical drill gun.

18. A method for providing visual guidance in a medical surgery, the method comprising:

registering, by a processor, a construct having at least one of a physical IM nail implant and a physical insertion handle within a virtual assistance device, wherein the registering comprising:
  scanning a first QR code attached to the physical insertion handle, and wherein the first QR code is sensed by the virtual assistance device, and wherein a virtual IM nail model creates a virtual impression of the physical IM nail implant and the physical insertion handle within the virtual assistance device;
registering, by the processor, a physical drill gun, the registering comprising:
  scanning a second QR code attached to the physical drill gun, wherein a drill gun model creates a virtual impression of the physical drill gun within the virtual assistance device;
registering, by the processor, through one or more third QR codes inserted on one or more holes provided over the physical IM nail implant for accepting screws during the medical surgery, coordinates of the one or more holes with respect to the coordinates of the virtual impression of the physical IM nail implant and the physical insertion handle; and
  wherein each of the virtual impression of the physical IM nail implant inside a target, the virtual impression of the physical drill gun, and the coordinates of the one or more holes are displayed on a user interface while inserting, each of the physical IM nail implant and the physical insertion handle into the target;
positioning, by the processor, the virtual impression of the physical drill gun over the virtual impression of the physical IM nail implant inside a target; and
aligning, by the processor, the virtual impression of the physical drill gun over the one or more holes based on the coordinates of the one or more holes registered within the virtual assistance device, wherein the aligning guides movement of the physical drill gun over the target in real-time while performing one or more surgical steps over the target through the physical drill gun.

\* \* \* \* \*